United States Patent [19]

Olmo et al.

[11] Plant 4,784

[45] Nov. 3, 1981

[54] TABLE GRAPE

[76] Inventors: Harold P. Olmo, Putah Creek Levee Rd.; Albert T. Koyama, 713 Hunt Way, both of Davis, Calif. 95616

[21] Appl. No.: 115,858

[22] Filed: Jan. 28, 1980

[51] Int. Cl.[3] ..... A01H 5/00

[52] U.S. Cl. ..... Plt./47

[58] Field of Search ..... Plt./47

*Primary Examiner*—James R. Feyrer

*Attorney, Agent, or Firm*—Townsend and Townsend

[57] ABSTRACT

A new and distinct variety of grapevine having the ability to produce early market seedless table grapes and very large raisins. The variety is further characterized by its unusually large berries with only occasional traces of seed development, a cluster that is naturally self-thinning at blossom time and its adaptability to short pruning methods.

3 Drawing Figures

This invention relates to a new and distinct variety of grapevine of the *vinifera* species to be used as an early market seedless table grape, as well as a very large raisin. The new variety is exceptional in two respects, having unusually large berries with only occasional traces of seed development and a cluster that is naturally self-thinning, saving materially on berry removal.

Figure 1:
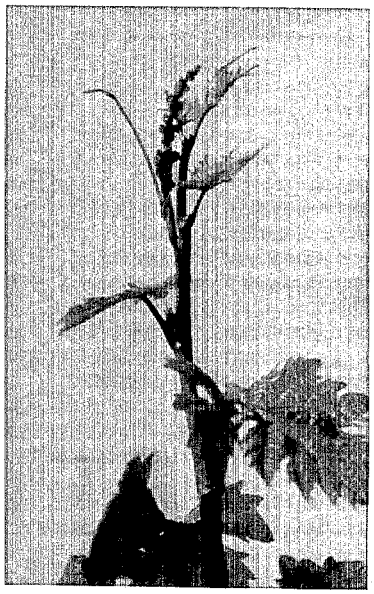
FIG. 1 is a drawing of a typical shoot tip of a plant of the new variety.
Figure 3:
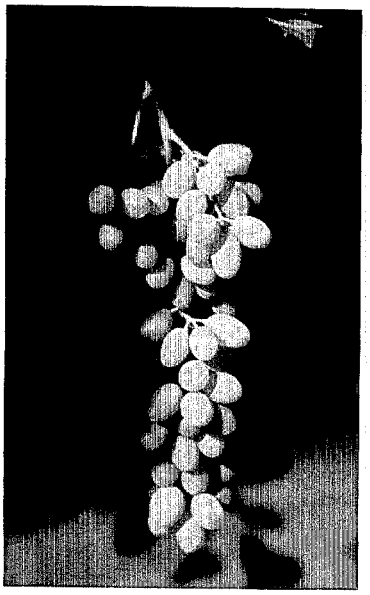
FIG. 3 is a drawing of a typical cluster of the new variety.
Figure 2:
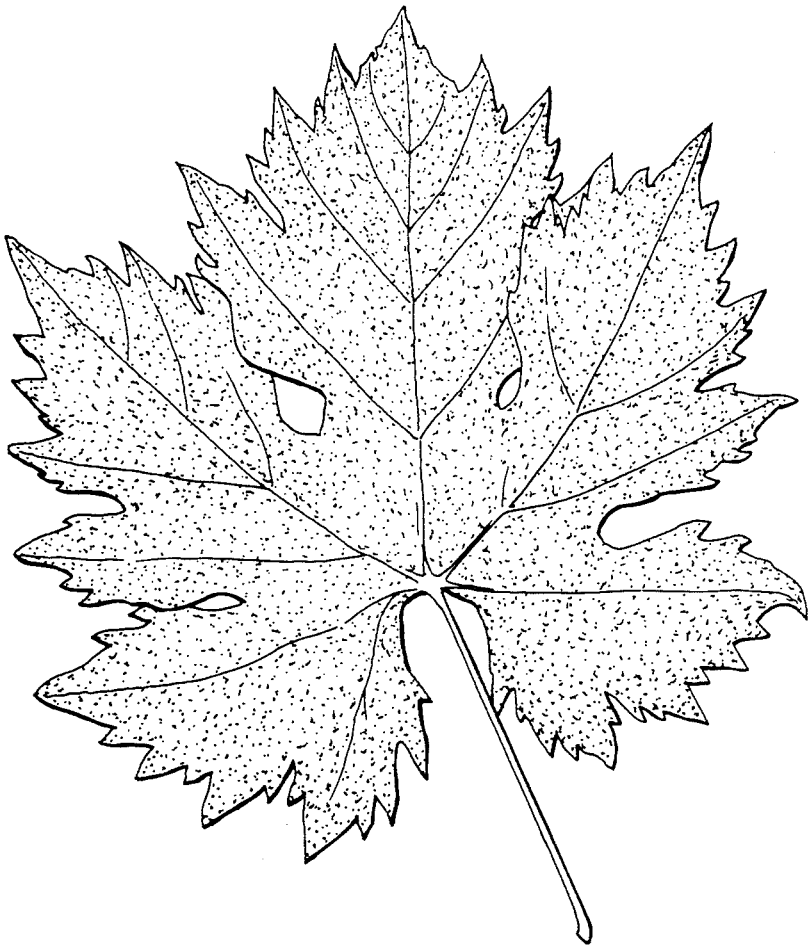
FIG. 2 is a drawing of a typical leaf of the new variety shown reduced from actual size.

The new variety results from the cross, Gold × Q25-6 (I7-42 × I7-11), made at the University of California vineyard, Davis, Calif., in 1966.

I7-11 and I7-42 are sister seedlings of the $F_1$ Emperor × Pirovano 75. The progeny of the cross consisted of 74 plants grown in the greenhouse at Davis and planted for fruiting at the Kearney Horticultural Field Station, Parlier, Calif. The vines first fruited in 1970 and the most promising seedling was identified as 31-123F, and later propagated for larger trials under this number. The first crop was noted as good, with loose clusters of large seedless berries, with tender skin and crisp berries. Some crop was harvested at 16° Brix on July 12, the remaining fruit reached 21.0° Brix on August 8.

The vine was asexually reproduced and multiplied by yema budding in the summer of 1970 on the rootstock Ganzin 1, at which time six vines were established for commercial trial. These vines retained the features of the original plant. The vines were trained on a lean-to trellis and pruned to bilateral cordons, the final form carrying six spurs to the side, pruned to two eyes per spur. This demonstrated another valuable characteristic of the variety, it was fruitful from basal buds and could be short-pruned instead of using the more expensive cane or "long" pruning required with Thompson Seedless.

The term yema is a Spanish word meaning eye or bud and refers to a method of grafting grapevines by inserting a bud of the fruiting variety onto the trunk of a rootstock vine already established in its permanent place in the vineyard. The operation is usually done in late summer, the bud is inserted just above ground level, is mounded over with soil and healed in place before winter. In the spring the grafted bud is uncovered, the top of the rootstock is cut off just above the union, and the bud pushes out and is trained up as the fruiting top.

Since the bud thus grafted has the advantage of a developed root system beneath it, a large vine can be produced in a short time. The method is also known in California as field budding.

The new variety, 31-123F, also underwent limited trials in the desert region of the Coachella Valley, in cooperation with the Desert Grape Growers League, beginning in 1971, but the ripening season was a week later than the Perlette. Irregular fruiting was evident because of too much growth and crowding, the vines not being trellised properly.

The colors referred to in the following description under the heading Plant Characteristics are subject to substantial variation and are not considered distinctive or diagnostic features of the plant of this invention.

PLANT CHARACTERISTICS

The varietal characteristics that distinguish this novel seedless grape have been observed since it first fruited in 1970 and observed thereafter in trial plots at Parlier and near Mecca in the Coachella Valley.

Vine: Vigorous, with sturdy and thick trunk, relatively few canes, heavy foliage canopy, budding out early, blossom and fruit-set 10 to 12 days before Thompson Seedless, adapted to short pruning on wide trellis, yield moderate, but high field packout of quality fruit possible, basal nodes fruitful.

Shoot Tip (10"–12"): Medium green with heavy bronzing, short nodes tapered, tip straight, arachnoid hairy, very leafy, hairy, but not felted. First young leaf (flat), very shiny, surface bullate, bronzed, three-lobed, teeth very narrow and very acute, glabrous, surface convoluted.

Shoot: Inflorescences borne at nodes 4 and 5, florets with dry calyptras, heavy shedding of flowers before fruit set, natural thinning.

Leaf: Large, 22.8 × 21.8 cm., glabrous, blade thick, broadly undulated; dark green above, light green below, with contrasting and prominent whitish ribs; cuneiform; central lobe square in outline, upper sinuses very deep, closely by overlapping lobes, lower sinuses wide U-shaped, half closed by overlap of lobes, petiolar sinus very wide, deep open U-shaped. Teeth in two series, very large, acute, some secondary teeth often as large as terminal ones of the lobes; petiole 11.8 cm. long, purplish-red over entire length.

Cane: Tapered, ellipsoidal or flattened in x-section, of medium length, light brown, but much darker at nodes, with several wide parallel striations of darker brown radiating from the position of the leaf scar; pith area small, circular, eye small, pointed.

Cluster: Primary cluster averages 486 gm., overall length 24.9 cm. from point of attachment, 11.8 cm. in width, 1.8 cm. to tendril plus 2.9 cm. to first lateral branch of rachis, cluster typically loose (some pedicels visible), to well-filled, average 124 berries per cluster, cluster stem reddish on exposed portions, woody only at base.

Berry: Very large for a seedless grape, ten largest berries per cluster average 2.5 × 1.6 cm., ovoid elongated, color is strong yellow green, 2.5 GY 9/8 to brilliant yellow green, 2.5 GY 9/8 (Nickerson Color Fan) when harvested in the Fresno area of the San Joaquin Valley, Calif. at commercial maturity, but berry color is rather dull, obscured by a heavy waxy bloom, skin thin but resistant to cracking, flesh firm, ripening early, ripens in Fresno, Calif. approximately three to four weeks before the usual September 1 picking date of Thompson Seedless, but one week after Perlette, higher in sugar and acid content than Perlette, at full maturity, with 19 to 21 percent soluble solids in the juice, a mild Muscat flavor can be discerned by only a few tasters, this flavor is more pronounced and evident in the cured raisins, mostly parthenocarpic with only slight traces of seed development that do not become flinty or brownish, adherence is very good and limited shipping tests indicate less berry shatter than Thompson Seedless under comparable conditions, skin is only moderately thick, but resistant to cracking, natural raisins of excellent quality have been produced by sun-drying in the vineyard row, however, the raisins may be too large for present commercial channels but may have interest as a snack food item.

Variety: The most distinctive feature of this new variety is the large size of the seedless berry with practically no traces of seed development, the self-thinning characteristic at blossom time resulting in a naturally loose or well-filled cluster and the early maturity and good palatability of the variety, and the adequacies of short pruning (cordon and spur) methods.

We claim:

1. The new and distinct variety of table grape herein described and illustrated and identified by the characteristics enumerated above.

* * * * *